United States Patent [19]
Washecheck et al.

[11] Patent Number: 5,328,883
[45] Date of Patent: Jul. 12, 1994

[54] HYDROCARBON CONVERSION

[75] Inventors: Don M. Washecheck, Naperville; Mark K. Barr, Wheaton; George A. Huff, Jr., Naperville; Mark P. Kaminsky, Winfield; Mark S. Kleefisch; Victor K. Shum, both of Naperville, all of Ill.

[73] Assignee: Amoco Corporation, Chicago, Ill.

[21] Appl. No.: 13,574

[22] Filed: Feb. 4, 1993

Related U.S. Application Data

[62] Division of Ser. No. 775,209, Oct. 11, 1991, Pat. No. 5,196,634.

[51] Int. Cl.$^5$ .............................................. B01J 23/00
[52] U.S. Cl. ................................... 502/303; 502/174; 502/302; 502/304; 502/341
[58] Field of Search ............... 502/174, 302, 303, 304, 502/341

[56] References Cited

U.S. PATENT DOCUMENTS 4,780,449 10/1988 Hicks .................................. 502/302

*Primary Examiner*—Patrick P. Garvin
*Assistant Examiner*—E. D. Irzinski
*Attorney, Agent, or Firm*—Scott P. McDonald; James R. Henes; Richard A. Kretchmer

[57] ABSTRACT

A contact material composition containing an intimately mixed, mixed oxide of at least one cationic species of a naturally occurring Group IIIB element, at least one cationic species of a Group IIA metal of magnesium, calcium, strontium, and barium and a cationic species of aluminum, as well as methods for hydrocarbon conversion using such contact material compositions are provided.

8 Claims, 1 Drawing Sheet

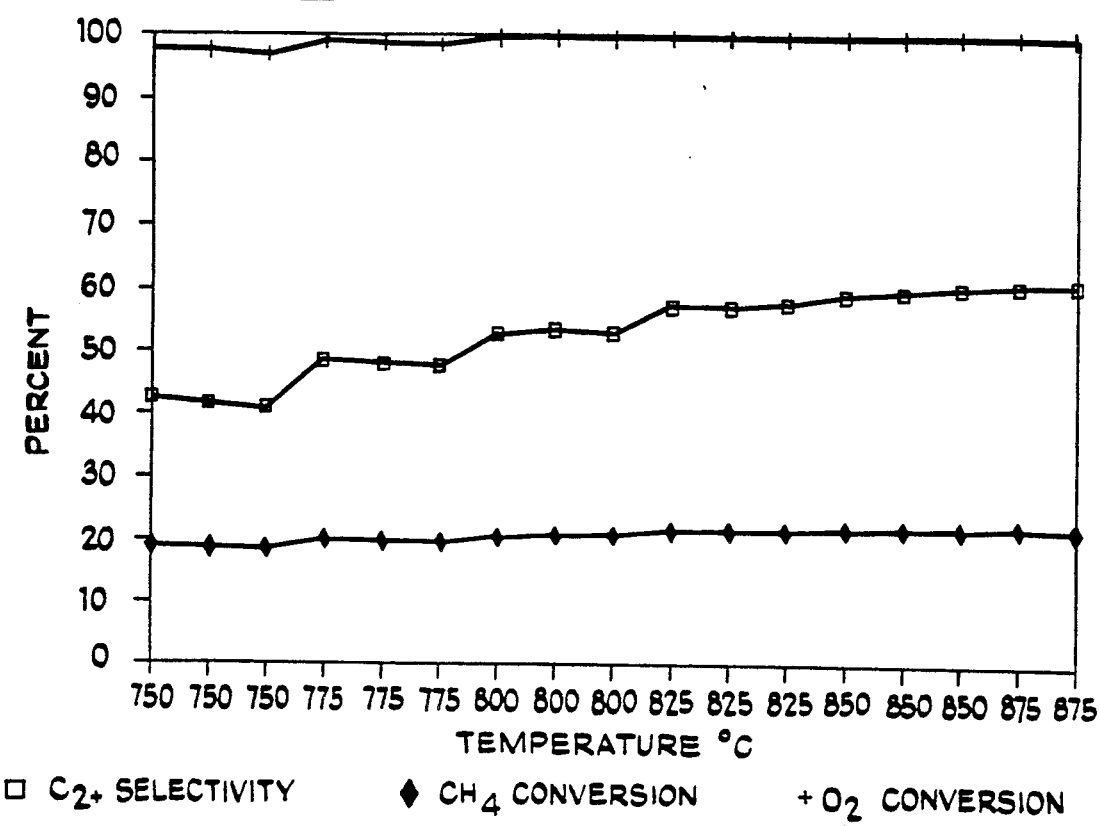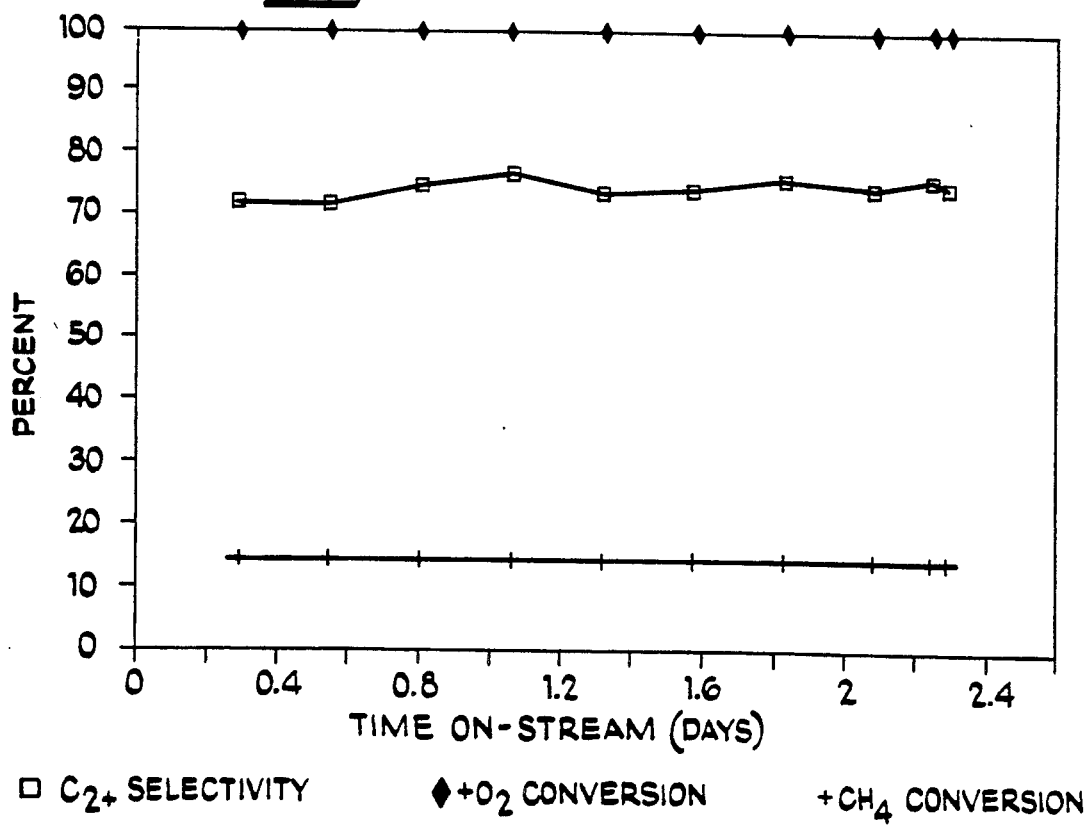

HYDROCARBON CONVERSION

This is a divisional of application Ser. No. 07/775,209, filed Oct. 11, 1991 and now U.S. Pat. No. 5,196,634.

BACKGROUND OF THE INVENTION

This invention relates generally to conversion of hydrocarbons and, more specifically, to contact material compositions and oxidative conversion processes using such compositions.

As the uncertain nature of the limited supplies of and access to crude oil has become increasingly apparent, alternative sources of hydrocarbons and fuels have been sought out and explored. The conversion of low molecular weight alkanes (lower alkanes) to higher molecular weight hydrocarbons has received increasing consideration as such low molecular weight alkanes may be generally available from more readily secured and reliable sources. Natural gas, partially as a result of its comparative abundance, has received a large measure of the attention that has focused on sources of low molecular weight alkanes. Large deposits of natural gas, mainly composed of methane, are found in many locations throughout the world. In addition, low molecular weight alkanes are generally present in coal deposits and may be formed during numerous mining operations, in various petroleum processes, and in the above- or below-ground gasification or liquefaction of coal, tar sands, oil shale and biomass, for example.

Today, much of the readily accessible natural gas generally has a high valued use as a fuel whether in residential, commercial or in industrial applications. Additional natural gas resources, however, are prevalent in many remote regions of the world, such as remote areas of Western Canada, Africa, Australia, U.S.S.R. and Asia. Commonly, natural gas from these remote resources is referred to as "remote natural gas" or, more briefly, "remote gas."

In many such remote regions, the widespread, direct use of the natural gas as a fuel is generally not currently profitable. Further, the relative inaccessibility of gas from such resources is a major obstacle to the more effective and extensive use of remote gas as the transportation of the gas to distant markets wherein the natural gas could find direct use as a fuel is typically economically unattractive.

Of course, while the primary current use of natural gas is as a fuel, natural gas may alternatively be used as a feedstock for chemical manufacture. In fact, natural gas is a primary chemical feedstock for the manufacture of numerous chemicals, such as methanol, ammonia, acetic acid, acetic anhydride, formic acid, and formaldehyde, for example. However, the markets for such chemicals are fairly limited in size. Consequently, methods for converting low molecular weight alkanes, such as those present in remote natural gas, to higher molecular weight hydrocarbons, preferably, to more easily transportable liquid fuels for which the world market is relatively large and/or elastic, are desired and a number of such methods have been proposed or reported.

Conversion of natural gas to liquid products is a promising solution to the problem of more effectively and efficiently utilizing low molecular weight hydrocarbons from remote areas and constitutes a special challenge to the petrochemical and energy industries. The dominant technology currently employed for the utilization of remote natural gas involves conversion of the natural gas to a liquid form via the formation of synthesis gas, i.e., a process intermediary composed of a mixture of hydrogen and carbon monoxide also commonly referred to as "syngas." In syngas processing, methane, the predominant component of natural gas, although typically difficult to activate, is reacted with oxygen or oxygen-containing compounds such as water or carbon dioxide to produce syngas which in turn is then converted to desired products.

Syngas processing, however, is relatively costly as the production of syngas and the subsequent conversion of the syngas are typically very capital intensive processing schemes. Further, while some of the products to which syngas can be converted, such as methanol, mixed alcohols, acetic acid, etc., contain oxygen and are thus logical products for production via syngas processing, hydrocarbon products such as gasoline and diesel fuel typically do not contain oxygen and consequently the production of such materials via syngas processing requires the additional processing step of oxygen removal. Consequently, when such products are produced via syngas processing, the addition and later removal of oxygen ultimately increases the cost of production.

When hydrocarbon products such as gasoline and diesel fuel are sought, the syngas mixture can be converted to syncrude, such as with Fischer-Tropsch technology, and then upgraded to the desired transportation fuels using typical refining methods. Alternatively, syngas can be converted to liquid oxygenates which can be blended with conventional transportation fuels to form materials such as gasohol, used as an alternative fuel or converted to conventional transportation fuels by catalysts such as certain zeolites.

Because syngas processing typically requires high capital investment, with syngas typically being produced in energy intensive ways such as by steam reforming where fuel is burned to supply the heat of reforming, and represents an indirect means of higher hydrocarbon production (i.e., such processing involves the formation and subsequent reaction of the syngas intermediaries), other means for converting lower alkanes directly to higher hydrocarbons have been sought.

Oxidative coupling has been recognized as a promising approach to the problem of conversion of lower alkanes to higher molecular weight hydrocarbons. The mechanism of action of oxidative coupling processing, however, has not been clearly identified or defined and is not clearly understood. In such oxidative coupling processing, a low molecular weight alkane or a mixture containing low molecular weight alkanes, such as methane, is contacted with a solid material referred to by various terms including catalyst, promoter, oxidative synthesizing agent, activator or contact material. In such processing, the methane is contacted with such a "contact material" and, depending on the composition of the contact material, in the presence or absence of free oxygen gas, is directly converted to ethane, ethylene, higher hydrocarbons and water. Carbon dioxide, the formation of which is highly favored thermodynamically, is an undesired product, however, as the formation of carbon dioxide results in both oxygen and carbon being consumed without production of the desired higher value $C_{2+}$ hydrocarbons.

Catalytic mixtures containing reducible metal oxides are highly active and many are 100% selective for producing CO₂, that is, they are combustion catalysts. In order to obtain desired selectivity for hydrocarbon formation, Group IA metals, particularly lithium and sodium, have been used in such catalytic mixtures. Under the conditions used for oxidative coupling, however, migration and loss of the alkali metal normally occurs. In order to avoid complete combustion, most methods for oxidative conversion have been carried out in the absence of an oxygen-containing gas, relying on the oxygen theoretically being supplied by the catalyst.

Nevertheless, in most cases involving oxidative coupling processing of methane, carbon monoxide and hydrogen are coproduced in addition to desired $C_{2+}$ hydrocarbons. If desired, such coproduced hydrogen can be used alone, in part or in its entirety, or supplemented with hydrogen from another source to effect conversion of carbon oxides to produce methane. Such produced methane can, in turn, be recycled for desired oxidative coupling processing. Alternatively, the hydrogen can be used to effect conversion of carbon monoxide to carbon-containing oxygenates such as methanol or mixed alcohols (e.g., a mixture of one or more alcohols such as methanol, ethanol, propanols and butanols) or higher hydrocarbons such as a mixture of paraffins and olefins typically produced in the process commonly known as Fischer-Tropsch synthesis. Alternatively or in addition, such coproduced carbon monoxide and hydrogen can, if desired, be combined with olefins, such as those produced during the oxidative coupling processing, to produce various oxygenates, such as propanol, for example. As described above, however, the production of materials such as oxygenates from carbon monoxide and hydrogen (i.e., synthesis gas) is not a direct approach for the utilization of natural gas, as such processing still involves the use of the syngas intermediaries.

Furthermore, the processing of coproduced hydrogen and carbon monoxide typically increases the cost of any such processing scheme. Thus, the need for active oxidative coupling contact materials which have relatively high selectivities for desired higher hydrocarbons and which contact materials are stable and have long life (i.e., maintain relatively high levels of activity and selectivity to higher hydrocarbons over extended periods of use without the need for regeneration or replacement).

Many patents describe processes for converting methane to heavier hydrocarbons in the presence of reducible metal oxide catalysts. During such processing, the reducible metal oxide "catalyst" typically is reduced and thus most of these patents require or imply the need for a separate stage to reoxidize the catalyst.

For example, U.S. Pat. No. 4,444,984 discloses a method for synthesizing hydrocarbons wherein methane is contacted with a reducible oxide of tin at an elevated temperature. Such contact results in the tin oxide being reduced. The reduced composition is then oxidized with molecular oxygen to regenerate a reducible oxide of tin.

U.S. Pat. No. 4,495,374 discloses the use of a reducible metal oxide promoted by an alkaline earth metal in such a method of methane conversion. During such processing, the reducible metal oxide of the promoted oxidative synthesizing agent is reduced. The reduced synthesizing agent can then be removed to a separate zone wherein it is contacted with an oxygen-containing gas to regenerate the promoted oxidative synthesizing agent.

Examples of other such patents include: U.S. Pat. No. 4,523,049, which shows a reducible metal oxide catalyst promoted by an alkali or alkaline earth metal, and requires the presence of oxygen during the oxidative coupling reaction; U.S. Pat. No. 4,656,155, which specifies a reducible metal oxide in combination with an oxide of zirconium, an oxide of yttrium and, optionally, an alkali metal; U.S. Pat. No. 4,450,310, which is directed to coupling promoted by alkaline earth metal oxides in the total absence of molecular oxygen; and U.S. Pat. No. 4,482,644, which teaches a barium-containing oxygen-deficient catalyst with a perovskite structure.

Several patents describe catalysts for higher hydrocarbon synthesis which can include a Group IIA; a metal of scandium, yttrium or lanthanum; and/or other metal oxides.

Commonly assigned U.S. Pat. No. 4,939,311 discloses a catalyst composition comprising a mixed oxide of:
a) a Group IIIB metal selected from the group consisting of yttrium, scandium and lanthanum;
b) a Group IIA metal selected from the group consisting of barium, calcium and strontium; and
c) a Group IVA metal selected from the group consisting of tin, lead and germanium, with the Group IIIB, Group IIA and Group IVA metals in an approximate mole ratio of 1:0.5–3:2–4, respectively.

U.S. Pat. No. 4,780,449 discloses a catalyst including metal oxides of a Group IIA metal, a Group IIIA metal, a lanthanide series metal excluding Ce, or mixtures thereof. The patent lists as optional promoter materials metal oxides of a metal of Groups IA, IIA, IIIA, IVB, VB, IB, the lanthanide series, or mixtures thereof.

Catalysts which contain metal oxides which are reduced under the reaction conditions of use are typically physically and/or chemically relatively unstable under the reaction conditions of use. That is, such catalysts generally do not maintain needed or desired physical and/or chemical characteristics for extended periods of time (e.g., such characteristics as reactivity and physical form are typically not maintained for more than a few minutes) without regeneration, reformation or other remedial procedures.

Also, as the reducible metal oxides of such materials typically undergo chemical reduction with use, the activity of the materials for producing desired products, such as $C_{2+}$ hydrocarbons in the oxidative coupling processing of methane, for example, worsen.

For example, with contact materials containing reducible metal oxides, the problem of over-reduction is typically associated with the reduction of the metal oxide to the metal. Often, the selectivity of the contact material changes dramatically when the material has been over-reduced, leading to a material which results in combustion reactions or which results in the formation of mixtures of carbon oxides with water and hydrogen when the material is used in the oxidative coupling of lower alkane such as methane, for example. Some reducible metal oxide-containing contact materials (e.g., manganese oxide) at temperatures in the range of about 800° to about 1,000° C. and in the absence of oxygen, once over-reduced are very difficult to reoxidize and a permanent or near permanent alteration in the characteristics of the material occurs. In some cases, the reduced metal can react with other materials in the composition to form a new phase which is difficult to reoxidize and the contact material is permanently damaged by over-reduction. Such alterations can, for example, result in a loss in selectivity to $C_{2+}$ hydrocarbons when the material is used in the oxidative coupling of methane.

Furthermore, contact materials containing metal oxides which are reducible under the reaction conditions of use can, in use, experience physical deterioration, e.g., breaking apart. Such physical deterioration results, at least in part, from changes in the material during oxidation and reduction. Frequently, the material in its various oxidation states has very different densities, e.g., the material contracts and swells as it is reduced and oxidized. The smaller particles or powders, frequently referred to as "fines," resulting when the material undergoes physical degradation results in pressure drop buildups (in fixed bed operation) and leads to loss of contact material (in fluid bed operation).

In fluid bed operation, fines are frequently carried out with the vapors from the reactor. Additionally, the fines are generally not easily separated from the product gases in common separating devices such as cyclones. Thus, costly separation techniques are required to effect separation of the fines from the product gases. The loss of contact material in the form of fines also necessitates the addition of more contact material to the process to replace that which has been lost and thereby increases the cost of such processing.

The search for a stable, long-lived contact material having high activity and selectivity in the oxidative conversion processing of hydrocarbons has continued.

SUMMARY OF THE INVENTION

The general object of this invention is to provide an improved contact material composition and improved methods for the oxidative conversion of hydrocarbons.

It is an object of the present invention to overcome one or more of the problems described above.

The general object of this invention can be attained, at least in part, through a composition including an intimately mixed, mixed oxide of:
  a) at least one cationic species of a naturally occurring Group IIIB element;
  b) at least one cationic species of a Group IIA metal of magnesium, calcium, strontium and barium; and
  c) a cationic species of aluminum.

The prior art fails to disclose or suggest stable contact material compositions containing an intimately mixed, mixed oxide of these cationic species. The stable contact material compositions of the invention by being able to maintain needed or desired physical and/or chemical characteristics for extended periods of time in use, permit the use thereof in processing without necessitating troublesome and/or costly remedial procedures.

The invention further comprehends a composition including an intimately mixed, mixed oxide of:
  a) at least one cationic species of a Group IIIB element selected from the group consisting of yttrium, lanthanum, neodymium, samarium and ytterbium;
  b) at least one cationic species of a Group IIA metal of strontium and barium; and
  c) a cationic species of aluminum.

The invention still further comprehends a composition including an intimately mixed, mixed oxide of:
  a) a cationic species of yttrium;
  b) at least one cationic species of a Group IIA metal of strontium and barium; and
  c) a cationic species of aluminum.

The invention also comprehends methods for the conversion of lower alkanes to higher molecular weight hydrocarbons. In such methods, a feed composition including at least one lower alkane species is contacted with the specified contact material composition. Such contacting is done in the presence of oxygen and at oxidative coupling reaction conditions.

The invention also comprehends methods for the oxidative dehydrogenation of dehydrogenatable hydrocarbons. In such methods, oxygen and a gas containing a dehydrogenatable hydrocarbon are contacted with the specified contact material composition at oxidative dehydrogenation reaction conditions to produce an effluent containing dehydrogenated hydrocarbons.

The invention also comprehends methods for the oxidative cracking of crackable hydrocarbons. In such methods, oxygen and a gas containing a crackable hydrocarbon are contacted with the specified contact material composition at oxidative cracking reaction conditions to produce an effluent containing cracked hydrocarbons.

As used herein, the term "reducible" is used to identify those oxides of metals which are reduced by contact with $C_1$-$C_3$ alkanes at temperatures within the range of about 500° C. to about 1,000° C.

The terms "dehydrogenatable hydrocarbons" and "crackable hydrocarbons" include not only conventional hydrocarbons, which contain exclusively hydrogen and carbon, but also compounds, which in addition to hydrogen and carbon, contain oxygen as well, e.g., compounds such as alcohols ($C_{2+}$ and $C_{3+}$ alcohols, for example).

The term "catalytically effective" refers to the ability of the material in question to increase chemical reactivity for the formation of hydrocarbons in preference to carbon oxide (CO and $CO_2$) formation.

The terms "oxide" and "oxides" include the various oxygen-containing compositions including hydroxides, carbonates, peroxides, superoxides and mixtures thereof, for example.

The term "lower alkane" as used herein refers to $C_1$-$C_3$ alkanes.

The term "contact material" as used herein refers to a material which:
  (a) when contacted with a lower alkane and oxygen at oxidative coupling reaction conditions results in the formation of hydrocarbons having a higher molecular weight than the original feed alkane, or
  (b) when contacted with a higher hydrocarbon (e.g., butanes, pentanes, hexanes and mixtures thereof) at oxidative dehydrogenation or oxidative cracking reaction conditions leads to a dehydrogenation and/or molecular weight reduction, respectively, of the higher hydrocarbon, generally with the formation of dehydrogenated lower molecular weight hydrocarbons.

The term "cofeed" operation as used herein refers to that mode of conversion operation wherein the contact material is simultaneously contacted by the feed material, e.g., feed hydrocarbon, and oxygen (such as in the form of an oxygen-containing gas). In such operation, the feed material and the oxygen can be mixed together before or during their contact with the contact material.

The term "redox" operation as used herein refers to that mode of conversion operation wherein the contact material is sequentially contacted by the feed material, e.g., feed hydrocarbon, followed by contact with oxygen (such as in the form of an oxygen-containing gas). In such operation, the feed material and oxygen are generally not mixed together to any substantial extent either before or during contact with the contact material. In some process designs, however, some such "carryover" or inadvertent mixing of the feed material and oxygen may occur.

The term "gasoline-type hydrocarbon products" as used herein refers to those hydrocarbons having a boiling point in the general range of $C_4$ hydrocarbons to about 450° F., inclusive.

The term "substantially free" as used herein to describe the contact material composition generally indicates that the contact material composition excludes amounts of the specified material(s) which materially affect the effectiveness of the contact material in the specified processing. While the affect of a specified material on the effectiveness of the contact material will, of course, be dependent on the material and processing involved, "substantially free" means that the contact material composition includes no more than nominal amounts of the specified materials, typically the composition contains an amount of no more than about 0.1 wt.%, more specifically the composition contains an amount of no more than about 100 ppm (0.01 wt.%) and more preferably the composition contains an amount of no more than about 50 ppm (0.005 wt.%) of the specified materials.

The term "intimately mixed" as used herein refers to mixing of the different contact material cationic species, either alone or in some compound form, on a molecular level. The term is descriptive of and refers to materials which when thin sectioned to about 90 nanometers or dispersed on a carbon film and scanned over a spot of no more than about 5 to 10 square microns, preferably a spot of no more than about 1 to 5 square microns and, more preferably, a spot of no more than about 0.1 to 1 square micron by way of Scanning Transmission Electron Microscopy with Energy Dispersive X-Ray Analysis (STEM-EDX) exhibits each of the three principal metal cationic species of the material in significant amounts (i.e., more than contaminant or impurity amounts).

Other objects and advantages of the invention will be apparent to those skilled in the art from the following detailed description taken in conjunction with the appended claims and figures.

BRIEF DESCRIPTION OF THE DRAWINGS

FIG. 1 is a graphical depiction of the percentage of $C_{2+}$ selectivity, $O_2$ conversion and $CH_4$ conversion, respectively, for selected operating temperatures using a contact material according to typical embodiments of the invention.

FIG. 2 is a graphical depiction of the percentage of $C_{2+}$ selectivity, $O_2$ conversion and $CH_4$ conversion, respectively, versus time on stream using a contact material according to a typical embodiment of the invention.

DETAILED DESCRIPTION OF THE INVENTION

According to the invention, a contact material composition and methods for hydrocarbon conversion are provided. The invention contemplates a contact material composition which is substantially free of catalytically effective reducible metal oxide and methods of hydrocarbon conversion utilizing such contact material compositions including:

a) methods for alkane conversion generally applicable to alkanes containing from 1 to 3 carbon atoms to form higher molecular weight hydrocarbons;
b) methods for dehydrogenation of dehydrogenatable hydrocarbons; and
c) methods for the cracking of crackable hydrocarbons.

In one preferred embodiment of the invention, methane, illustrative of a lower molecular weight alkane feedstock useful in the practice of the invention, is mixed with air, as a source of oxygen, and the resulting mixture is contacted with a suitable contact material, as described below, for the oxidative coupling of the aforesaid alkane. Thus, the invention will be described herein with reference to conversion wherein the lower alkanes converted to higher molecular weight hydrocarbons comprise methane. It is to be understood, however, that feedstocks typically useful in the practice of the invention will include lower alkanes such as methane, ethane or propane (i.e., $C_1$–$C_3$ alkanes) either alone, separately or in mixtures with each other, with or without the presence of other materials, such as inert gases, e.g., $N_2$ or minor amounts of other hydrocarbon materials, for example. Natural gas is an example of a feedstock for use in the practice of at least some aspects of the invention. It being understood that natural gas, while containing predominantly methane, can and typically does contain at least minor amounts of the other above-identified lower alkanes as well as other materials such as nitrogen gas and carbon dioxide, for example. Also, it is to be understood that the method can be utilized with higher alkane feedstocks. As a result of competing reaction kinetics, however, such use can result in a reduction in the amount of higher molecular weight hydrocarbons formed thereby.

It is also to be understood that in the hydrocarbon conversion methods of the invention, sources or forms of oxygen-containing gas other than air can be used or preferred. Thus, the oxygen-containing gas for use in the conversion methods of the invention can vary in molecular oxygen content from oxygen-depleted air, to air, to oxygen gas itself, for example. Air or enriched air can be a preferred source of molecular oxygen.

Such oxidative coupling processing of methane, when air is used as a source of oxygen, typically results in a gaseous mixture comprising ethane and ethylene, illustrative of saturated and unsaturated aliphatic hydrocarbon products having higher molecular weights than the feedstock alkanes from which they were formed, and possibly some traces of aromatics or higher hydrocarbons which may form in the reactor, such as at high operating temperatures, for example, at temperatures greater than 750° C., as well as carbon monoxide, carbon dioxide, nitrogen, water, any remaining unreacted feedstock alkane and oxygen. It being understood that conventional catalytic processing schemes, such as refining hydrotreatment, are typically conducted at operating temperatures of only about 400° C. to 450° C.

Such a reaction product mixture may illustratively be used as chemical feedstock or be further reacted, such as occurs during conversion, to form gasoline type hydrocarbon products. For example, the effluent with desired or required pretreatment, e.g., $H_2O$ removal, and/or downstream treatment, e.g., $N_2$ removal, may be passed over a suitable aromatization/oligomerization catalyst (such as a crystalline borosilicate or aluminosilicate molecular sieve material or supported phosphoric acid) to produce desired gasoline-type hydrocarbon products. Other specific uses of the reactor effluent will be apparent to those skilled in the art.

In the above-described embodiment, methane and oxygen (as a part of air) are simultaneously contacted with the contact material. Such operation is commonly referred to as "cofeed" operation and in such operation, oxygen, which may be needed for the coupling reaction to occur, is also fed to the reactor rather than exclusively being carried into the reactor via the lattice of the contact material, as may be typical of "redox" operation, as described above. Further, cofeed operation may minimize or eliminate the need for subsequent reoxidation of the contact material such as may be required to resupply lattice oxygen to contact materials such as those which typically contain reducible metal oxides as typically is required when such contact materials are utilized in a redox mode operating scheme.

Generally, a suitable feedstock for the method of this invention comprises at least one of methane, ethane and propane and preferably comprises mostly methane, e.g., at least about 75 percent methane, and more preferably may be methane as methane is typically the predominant hydrocarbon reserve component which is desired to be converted to a higher molecular weight hydrocarbon. Thus, a suitable feedstock for the method of this invention comprises natural gas, gases formed during mining operations and petroleum processes or in the above- or below-ground gasification or liquefaction of coal, tar sands, oil shale and biomass, for example.

The contacting of the hydrocarbon feedstock with the oxygen-containing gas and in the presence of the contact material generally is performed at oxidative coupling reaction conditions including temperature and pressure. Preferably, such contacting is performed at a temperature in the range of from about 600° C. to about 1,000° C. and, more preferably, in the range of from about 700° C. to about 900° C. These temperature ranges have been found to be preferred as operation at temperatures below about 600° C. may generally result in the contact material having relatively unfavorable product (e.g., $C_{2+}$ hydrocarbons) selectivities while operation at higher temperatures, e.g., temperatures greater than about 900° C., can result in generally undesirable thermal reactions seriously competing with coupling reactions. The products resulting from such thermal reactions will typically be largely comprised of $H_2$, $CO_x$ (where x = 1 or 2) and may also include coke, acetylene and aromatics such as benzene, for example. Such thermal reactions will typically overwhelm the desired coupling reactions when temperatures exceed about 1,000° C. It is to be understood, however, that at higher reaction temperatures at least trace quantities of aromatic compounds may also form.

The contacting of the hydrocarbon feedstock and oxygen with the contact material is preferably performed under a total absolute pressure in the range of from about 0.1 atmosphere to about 10 atmospheres, and more preferably in the range of from about 1 atmosphere to about 5 atmospheres, as operation at pressures exceeding this range typically results in reduced $C_{2+}$ product selectivities while subatmospheric operation is believed to be economically unattractive as capital expenditures escalate rapidly for a system to be capable of handling the actual volumes of gas required for such a commercial operation.

The ratio of the partial pressure of the combined feedstock alkanes containing from 1 to 3 carbon atoms to the oxygen partial pressure at the entrance of the reactor in the contacting step is preferably in the range of from about 2:1 to about 40:1 and, more preferably, in the range of from about 2:1 to about 10:1, as operation at lower $C_1$-$C_3$ alkane to oxygen partial pressure ratios generally results in excessive carbon oxide formation, while operation at higher ratios may result in insufficient amounts of oxygen being present to obtain desired levels of conversion and consequently results in the remainder of greater amounts of unreacted hydrocarbon reactant. The combined partial pressures of the alkanes in the feedstock containing from 1 to 3 carbon atoms at the entrance to the first reactor (the contacting reactor) is preferably no more than about 10 atmospheres, and, more preferably, no more than about 4 atmospheres. The oxygen partial pressure at the entrance to the first reactor is preferably no more than about 4 atmospheres and, more preferably, no more than about 2 atmospheres. The oxygen partial pressure in the gaseous effluent from the reactor in the contacting step is preferably substantially 0.

In view of the highly active nature of the subject contact materials for the oxidative conversion of lower alkanes to a product composition containing higher molecular weight hydrocarbons, the contacting step is preferably performed at a space velocity of from about 1,000 to about 1,000,000 volumes of total feed gas at ambient conditions per volume of catalytic composition per hour and more preferably at a space velocity of about 50,000 to about 200,000 volumes of total feed gas per volume of catalytic composition per hour, as thermal reactions will generally predominate with operation at lower space velocities while oxygen conversion will generally be unsuitably incomplete with operation at higher space velocities.

The high activity of the subject contact materials combined with the large heat release associated with the exothermic oxidative coupling reaction of lower alkanes, makes heat transfer and temperature control significant engineering challenges to commercial operation of the process. Reactors particularly suited for use in the practice of the invention need to allow for heat transfer and to permit desired temperature control. Such reactors can include fluidized bed reactors wherein the contact material is finely divided as this promotes a more rapid heat transfer as well as tubular reactors wherein the contact material is directly applied to the reactor wall to promote heat transfer and to permit desired temperature control.

The present invention provides an intimately mixed contact material composition substantially free of catalytically effective reducible metal oxide and containing at least three different cationic species. In its broader aspects, the contact material composition of this invention comprises, consists of, or consists essentially of an intimately mixed, mixed oxide containing:

a) at least one cationic species of a naturally occurring Group IIIB element;
b) at least one cationic species of a Group IIA metal selected from the group consisting of magnesium, calcium, strontium and barium; and
c) a cationic species of aluminum.

It has been found that materials with an intimate mixture of at least 1 cationic species of a Group IIIB and at least 1 cationic species of a Group IIA metal, selected from the group consisting of magnesium, calcium, strontium and barium, have improved performance characteristics, e.g., higher $C_{2+}$ selectivities when used in the oxidative coupling processing of methane, as compared to the corresponding contact materials wherein the Group IIIB species and the Group IIA species are used alone or in which the species are present in a non-intimately mixed fashion.

It has been further found that a cationic species of aluminum in the intimate mixture results in a contact material with improved stability and improved physical properties such as improved hardness and attrition resistance, ss is desired when fluidizable contact materials are sought, as compared to similar materials but which do not contain an intimately mixed aluminum species.

Such compositions will preferably contain about 2 to 20 weight percent aluminum and, more preferably, will contain aluminum in an amount in the range of 5–10 weight percent of the contact material composition (such weight percents being on an elemental basis). Such relative amounts of aluminum are generally preferred as such compositions will generally exhibit desired chemical and physical stability, as well as desired reactivity and selectivity. For example, and without wishing to be bound by any theory or mode of operation, it is believed that compositions containing only lesser relative amounts of aluminum do not result in sufficient chemical interaction to minimize or avoid the loss of other composition elements or sufficiently contribute to the hardness of the resulting composition, e.g., chemical and physical stability, respectively.

In addition, those compositions containing aluminum, typically present as the oxide, in higher relative amounts, can have an adverse effect on the reactivity and/or selectivity of the composition. For example, the higher relative amount of aluminum can dilute the relative amounts of other composition components to such an extent that the reactivity of the composition is reduced.

Another factor which limits the relative amount of aluminum in these compositions is the effect of incorporation of aluminum as the oxide on the surface area of the composition. Generally, when the surface area of the contact material becomes too great, e.g., greater than about 150 $m^2/g$, more particularly greater than about 50 $m^2/g$ and even more particularly greater than about 20 $m^2/g$, such as can occur when the alumina content of the material is too high, the selectivity of the composition is significantly and dramatically altered. For example, when used in oxidative coupling of lower alkanes, the use of a contact material composition with too large of a surface area generally leads to increased formation of carbon oxides, as opposed to the formation of additional desired higher hydrocarbons. Further, when used in oxidative dehydrogenation or oxidative cracking of higher hydrocarbons, the use of a contact material composition having too large a surface area can result in increased carbon deposition on the contact material.

Carbon deposition not only results in the loss of carbon from the feed by the formation of undesired products, e.g., coke, it can also result in a loss of activity for the contact material. For example, when using a fixed bed reactor, as the activity of the contact material decreases because of increasing carbon deposition, the process periodically must be interrupted and the contact material regenerated by the removal of some of the carbon formed thereon, such as by the oxidation of the carbon. Of course, such periodic regenerations of the process results in a loss of process productivity. Further, during the removal of the carbon such as by an exothermic process, the contact material can be damaged by reaching elevated temperatures in sections or areas during the regeneration. Such sections or areas of high temperature are commonly referred to as "hot spots." Hot spots can irreversibly damage the contact material such as through sintering and result in a loss in activity, selectivity or physical strength for the material. Alternatively, when the process uses a fluid bed of contact material and the material experiences a loss of activity as a result of carbon deposition, the material generally will be continuously removed from the reactor vessel to permit the removal of the carbon from the contact material in a separate vessel, e.g., a regenerator. If the amount of the carbon deposition on the contact material is excessive, heat balancing of the process can be difficult to achieve and control. Regardless of the type of reactor used, carbon deposition can also lead to a loss of physical strength in the contact material.

Also, in such compositions, the cationic species of the Group IIIB element and the Group IIA metal are preferably present in an approximate molar or atomic ratio of about 1 to about 0.5–3 and, more preferably, in a ratio of about 1 to about 2.

In one preferred embodiment of the invention, the Group IIIB element is selected from the group consisting of yttrium, lanthanum, neodymium, samarium and ytterbium, as Group IIIB elements which form oxides that do not have a +4 oxidation state. Our experience has been that accessibility to a higher oxidation state, e.g., an oxidation state of +4, leads to contact materials which have poorer selectivity and are more susceptible to reduction, e.g., are susceptible to reduction to a +3 oxidation state, i.e., are reducible metal oxides, and can thus lead to loss of physical strength or lead to increased carbon oxide formation.

In a particularly preferred embodiment, the Group IIIB element cationic species is yttrium, at least in part because of the comparative general availability of yttrium.

In one preferred embodiment of the invention, the Group IIA metal cationic species will be either strontium or barium, as contact materials containing strontium or barium generally exhibit a greater selectivity to higher hydrocarbons when the materials are used in oxidative coupling of lower alkanes, as compared to similar compositions which instead contain other Group IIA metals or no Group IIA metals at all. The greater selectivity of the subject compositions containing strontium or barium is believed, at least in part, to result from strontium and barium having a preferred ionic size and basicity as compared to the other Group IIA metals. It is believed that the ionic size of strontium and barium, as being generally more similar to Group IIIB metals, facilitates their incorporation into the material. In addition, basicity is believed to contribute to the ability of the resulting contact material to perform such as in the ability of the contact material to abstract hydrogen from the methane molecule in the oxidative coupling of methane, for example.

One preferred composition of the invention comprises a mixed oxide of cationic species of a) yttrium, b) strontium or barium, and c) aluminum, with such compositions containing aluminum in an amount of about 2 to 20 weight percent and, more preferably, about 5 to 10 weight percent of the contact material composition and with yttrium and the strontium and/or barium being present in an approximate molar or atomic ratio of about 1 to about 0.5–3 and, more preferably, in a ratio of about 1 yttrium to about 2 of the Group IIA metal.

The contact materials of the invention may be prepared by any suitable method. Generally speaking, a preparation method wherein a component comprising a Group IIIB element cationic species (e.g., yttrium), a component comprising a Group II metal cationic species (preferably strontium or barium) and a component comprising aluminum cationc species (e.g., alumina) are mixed and suitably calcined to form an appropriately homogeneous material will be utilized.

The precursor materials resulting from these preparation techniques will typically be calcined at a temperature and for a duration sufficient to lead to a stabilizing interaction among the principal metal cations of the material, whereby solid state transformations typically occur and the material becomes more homogeneous, e.g., "intimately mixed." For example, the precursors can be calcined at 800° C. for 8 to 12 hours. In such a preparation, the mixing of the components can be characterized as being on a microscopic scale (e.g., about 100 micron particle size) and with the components interacting to stabilize and form compound(s) containing more than one of the cationic species, such as barium aluminate with yttria incorporated therein, for example.

In one preferred method of preparation, a yttria sol or colloid is mixed with an alumina sol and to which mixture a barium hydroxide base is added to form a gel which is dried and calcined. It is to be understood that the substitution of very fine powders or the mixing of fine powders of salts of any or all the cationic species with powders or colloids of the other cationic species of the composition can and generally will also lead to the desired stabilizing interaction among the constituents of the material upon calcination. Further, it is to be understood that such stabilizing interaction can, for example, also be achieved through exposure of a precursor of the contact material to the high temperatures associated with the use of the material compositions in processing, such as in the oxidative conversion of lower molecular weight alkanes to higher molecular weight hydrocarbons wherein such stabilizing reaction can be achieved in situ, in the reactor, by means of the exposure of a material precursor to the reaction conditions.

The subject compositions by being substantially free of catalytically effective reducible metals are not susceptible to over-reduction or over-oxidation and the difficulties associated with such changes, as are those compositions containing reducible metal oxides. In addition, the subject contact material compositions are sufficiently hard so that they can be used to form a material that can be fluidized without large losses of material in the form of fines.

The contact materials of the invention can also be used in oxidative conversion processes to produce dehydrogenated and/or lighter products.

One such application for the compositions of the invention is the oxidative dehydrogenation of dehydrogenatable hydrocarbons and compounds, specifically processing in which the carbon framework of the hydrocarbon feedstock is substantially retained but with the removal of hydrogen therefrom. The process comprises contacting a feedstock, e.g., a gas, comprising a dehydrogenatable hydrocarbon or compound with oxygen in the presence of the subject contact material to produce dehydrogenated hydrocarbons and coproduct water. Carbon oxides, i.e., CO and $CO_2$, and hydrogen can also be formed as by-products of the overall reaction, it being understood that hydrogen by-product can also be formed as a result of water-gas shift reaction.

Dehydrogenatable hydrocarbons include a wide variety of hydrocarbons including $C_{2+}$ alkanes, cycloalkanes, olefins, alkylaromatics, etc., for example. As used herein, dehydrogenatable hydrocarbons are understood to also include various forms of oxygen-containing hydrocarbons such as alcohols (e.g., methanol, ethanol, propanol and butanols) and aldehydes (e.g., ethanol, propanol and butanol) and mixtures thereof with and without other dehydrogenatable hydrocarbons.

The dehydrogenated product depends in part on the feedstock selected. For example, alkanes can be dehydrogenated to form olefins, diolefins, alkynes, etc., olefins can be dehydrogenated to form diolefins, alkynes, etc., aldehydes can be dehydrogenated to form unsaturated aldehydes and alcohols can be dehydrogenated to form aldehydes, for example. One preferred class of feedstock comprises $C_2$-$C_6$ alkanes. One preferred process embodiment comprises oxidative dehydrogenation of $C_2$-$C_6$ alkanes to form corresponding mono-olefins.

Conditions for oxidative dehydrogenation processing include an operational temperature generally lower than the temperatures preferred for oxidative coupling processing. For example, the temperature for oxidative dehydrogenation processing is generally preferably in the range of about 300° C. to about 650° C. whereas temperatures for the oxidative coupling of methane are typically preferably greater than 700° C. Operating pressures are not narrowly critical and can range from subatmospheric to pressurized operation. In addition, and at least in part as a result of operation at lower operating temperatures, operating pressures for oxidative dehydrogenation can be greater than the pressures preferred for the oxidative coupling of lower alkanes such as methane, for example. Lower operating temperatures typically can result in decreased gas phase reaction contributions. Gas phase reactions often are free radical in nature. The collision of radical species with oxygen in the gas phase, however, often leads to the undesirable formation of carbon oxides. While increasing the pressure increases the frequency of gas phase collisions, to the extent that gas phase reaction contributions are decreased as a result of lower operating temperatures usable in oxidative dehydrogenation, the pressure can be increased without a deleterious increase in carbon oxides formation. Generally, for economic reasons, operational pressures of a few hundred pounds per square inch will be preferred for oxidative dehydrogenation processing, as pressures in this range are generally more conducive to economical separation processing and for the optimization of compressor operation and cost.

In oxidative dehydrogenation processing, the ratio of the partial pressure of the dehydrogenatable hydrocarbon feedstock to the partial pressure of the feed oxygen is preferably in the range of from about 0.5:1 to about 40:1 and, more preferably, in the range of from about 1:1 to about 20:1.

The lower limit of the ratio of hydrocarbon feedstock to feed oxygen is generally limited by the flammability range for the feed blend. While some fluid bed reactors can operate with flammable feed blends, such operation is generally undesirable due to safety concerns. In turn, as low conversions per pass typically results in either the unproductive use of feed or to the typically costly recycle of unreacted feed, the upper limit of hydrocarbon to oxygen ratio is generally limited by the need to attain acceptable per pass conversion rates of feed.

As compared to conventional dehydrogenation processing, oxidative dehydrogenation processing advantageously can result in higher conversions, operate at higher pressures without thermodynamic considerations limiting the conversion per pass, generally proceeds through exothermic reactions and is not limited by coke formation as is typically found in conventional dehydrogenation processing. In addition, the exothermic nature of the reactions involved in oxidative dehydrogenation processing can provide at least a significant portion of the heat necessary to bring the reactants up to the desired operating temperature and keep the reactants at the operating temperature during reaction, thus simplifying the heat transfer equipment needed in the operation of the process.

Conventional dehydrogenation is limited by thermodynamic considerations and typically results in the production of hydrogen and a dehydrogenated product. The amount of hydrogen present limits the equilibrium conversion to dehydrogenated product since hydrogen and the dehydrogenated product can react, e.g., rehydrogenate the dehydrogenated product. As conventional dehydrogenation reactions are generally endothermic in nature, increasing the system operating temperature can serve to reduce the effect of such an equilibrium limitation. As the endothermic reactions occur, the temperature in the system decreases until an equilibrium limitation is reached. Significant process system complications result when the operating system is required to provide the amounts of heat required to counter equilibrium limitations and the endothermic nature of the conventional dehydrogenation reaction. In addition, as the system operating temperature is increased, the amount or extent of carbon or coke formation in such processing can become more significant. Consequently, most commercial conventional dehydrogenation processes involve coke removal steps which are typically relatively costly.

While the oxidative dehydrogenation processing of the invention does not result in significant coke formation, the processing does produce at least some carbon oxides. Generally, conventional dehydrogenation processing does not produce such carbon oxides. In the manufacture and production of transportation fuels or fuel additives, the carbon oxides and hydrogen coproduced with the dehydrogenated products can be used or further processed, such as through Fischer-Tropsch processing, such as is applicable to the processing of synthesis gas (also commonly referred to as "syngas"), e.g., a mixture of $H_2$ and CO, with or without the presence of $CO_2$. Furthermore, for continuous operation of non-chemical grade olefin production, such as in the manufacture of fuel components, carbon oxide formation is much preferred over coke formation and the problems attendant coke removal processing.

Another specific application for the compositions of this invention is the oxidative cracking of crackable hydrocarbons and compounds. The process comprises contacting a gas or liquid comprising a crackable hydrocarbon or compound with oxygen in the presence of the subject contact material to produce cracked hydrocarbons/compounds. In addition, water and carbon oxides (i.e., carbon monoxide and/or carbon dioxide) as well as some hydrogen, will also typically be produced.

Crackable hydrocarbons include a wide variety of hydrocarbons including $C_3+$ alkanes, cycloalkanes, alkyl aromatics, etc., for example.

The cracked product depends, in part, on the feedstock selected. Usually, the cracked product will contain olefinic hydrocarbons, e.g., molecules having carbon-carbon double bonds. One preferred class of feedstock comprises $C_3-C_6$ alkanes. One preferred process embodiment comprises oxidative cracking of $C_3-C_6$ alkanes to form a cracked product including ethane, ethene, propane, propene, butane and butenes, for example.

Oxidative cracking processing differs significantly from conventional steam cracking processing. Primary areas of difference include heat balances, the formation of carbon oxides and desired unit operation conditions. For example, oxidative cracking processing is an exothermic process which can provide heat needed to raise the temperature of the reactants to the desired cracking operating temperature and to keep the reactants at a desired temperature range during processing, thus simplifying the heat transfer equipment needed for such processing. Generally, oxidative cracking processing has an operational temperature towards the higher end of the operational temperature range for oxidative dehydrogenation processing but less than that of oxidative coupling processing. For example, the operational temperature for oxidative cracking processing is generally preferably in the range of about 450° C. to about 650° C. with an operational temperature in the range of about 500° C. to about 550° C. being generally more preferred.

In addition, oxidative cracking is an exothermic process. The heat so generated can be used to heat the reactants to the desired operating temperature and keep the reactants at the operating temperature during reaction, thus simplifying the heat transfer equipment needed in the operation of the process. Generally, the hydrocarbon to oxygen ratios for use in oxidative cracking processing are in the same general range as those previously identified for use in oxidative dehydrogenation processing and are typically limited by the same factors of flammability limits and the economic need for an adequate per pass conversion rate.

In addition, other forms or modes of hydrocarbon cracking typically result in the formation of coke. Generally, such coke can act to foul heat exchange surfaces, e.g., in conventional tubular cracking reactors, coke fouling the heat exchange surfaces generally will serve to decrease the rate of heat transfer. Also, as detailed above, carbon/coke formation and the removal of such carbon/coke typically results in a loss in process productivity. In contrast, in oxidative cracking processing, carbon oxides are formed as opposed to carbon/coke formation. The carbon oxides so formed can be processed as addressed above in the description of oxidative dehydrogenation.

In addition, conventional hydrocarbon cracking processing typically results in the production of hydrogen and a cracked hydrocarbon product. The amount of hydrogen present limits the equilibrium conversion to cracked product. Conventionally, high temperatures are used to overcome such equilibrium limitations and to increase the reaction rate. Associated with such higher temperature operation, however, is increased coke formation. Also, increasing reactor pressure in a conventional cracking reactor leads to increased equilibrium limitations since, for conventional cracking, the volume of products is typically greater than the volume of reactants.

Since the oxidatively driven reactions are not as limited by equilibrium considerations, oxidative cracking processing can be operated at higher pressures than conventional cracking reactions. Higher pressures, such as operating pressures of a few hundred pounds per square inch, are desirable as such high pressures can result in increased efficiency in operating downstream separation processes and in matching desirable operating pressures for downstream conversion processes. Preferred operating pressure ranges generally range from about 0.5 atmospheres absolute to about 100 atmospheres absolute, with operating pressures in the range of about 2 to about 50 atmospheres absolute generally being more preferred. It is understood that the operation of gas reaction processes at elevated pressures results in reducing the size of processing vessels required and thus generally reduces the cost of the vessels and of the associated equipment for compression of products. In cracking processing, the volumes of cracked products as gases are greater than the volumes of the reactants as gases. In such processing, it is generally less expensive to compress the reactants and operate the reactor under pressure rather than compress the gases from a lower pressure reactor.

As will be appreciated from the above discussion of dehydrogenated products resulting from the oxidative dehydrogenation of a dehydrogenatable hydrocarbon and cracked products resulting from the oxidative cracking of a crackable hydrocarbon, such dehydrogenated products can and frequently do contain at least some cracked hydrocarbons and such cracked products can and frequently do contain at least some dehydrogenated hydrocarbons.

It is also to be understood that the contact material of the invention can also have applicability in non-oxidative dehydrogenation and non-oxidative cracking, that is in dehydrogenation and cracking in the substantial absence of oxygen. Such non-oxidative processing is generally under similar reaction conditions as those generally stated above for corresponding oxidative conversion processing.

The contact materials and the processes utilizing the subject contact materials illustratively disclosed herein can suitably be practiced in the absence of any component or ingredient or process step, respectively, which is not specifically disclosed herein.

The present invention is described in further detail in connection with the following examples which illustrate various aspects involved in the practice of the invention. It is to be understood that all changes that come within the spirit of the invention are desired to be protected and thus the invention is not to be construed as limited by these examples.

EXAMPLES

Comparative Example 1

$YBa_2$ on alumina support

Twenty grams of a fluidizable alpha alumina (UCI-SHAT-99-16) was calcined for 1 hour at 500° C. Yttrium acetate tetrahydrate, 0.840 grams, was dissolved in water to form a solution. Barium acetate, 0.967 grams, was dissolved in the solution and the resulting solution was diluted to 5.6 cc total volume. This solution was added to the dried alumina support under a partial vacuum and then dried at 120° C. The dried material was calcined at 800° C. for 4 hours. (Notes: nominally 0.85 wt. % Y, 2.5 wt. % Ba, which corresponds to about 2 Ba to 1 Y on a mole basis)

Comparative Example 2

The catalyst of Comparative Example 1 was tested for methane partial oxidation.

A 0.5 gram portion of the catalyst produced in Comparative Example 1 was diluted with 1.00 gram of 30–50 mesh low surface area alpha alumina material and loaded in a quartz reactor, forming a catalyst zone. A feed gas blend of 30% methane, 6% oxygen, and balance of nitrogen was passed over the catalyst at 100 standard cc per minute to give a relative feed rate of 12,000 cc-gas per hour per gram of catalyst. Temperature of the catalyst zone was controlled to 850° C.

Results:

Initial oxygen conversion of the catalyst was 65% but decreased quickly to about 38%. Selectivity for $C_{2+}$ hydrocarbons at 38% oxygen conversion was about 58% with the hydrocarbons being primarily ethane and ethylene. The balance of the carbon-containing products were carbon oxides.

EXAMPLE 1

Preparation of a sol-gel mixture, contact material having the nominal composition $YBa_2AlO_x$, where x=a molar amount necessary for the contact material composition to be at stoichiometric balance for the nominal composition, x=5.

A PHF alumina sol (56.3 grams) containing about 9 weight percent alumina was mixed with 100 cc of water. To this mix, 80.7 grams of a yttria collid (from Hydrocol Corp.) containing about 14 weight percent yttria was added and mixed. During the addition and mixing, no formation of a precipitate was observed.

Barium hydroxide octahydrate, (63.3 grams) was placed in 200 cc of water to form a solution and heated to about 40° C. to 60° C. to aid in the dissolution of the barium hydroxide octahydrate. The barium-containing solution was added to the yttria alumina mix and a thin gel formed. The gel was put in a vacuum oven with 40 inches of vacuum with a small air purge and with the oven set at 120° C. for overnight.

The dried material was put in an air-purged muffle furnace at room temperature. The temperature setting on the furnace was set to 800° C. and the material was left in the furnace for 3 hours. (Note: The furnace tool about 30 minutes to achieve an internal temperature of 800° C.)

EXAMPLE 2

Testing of the contact material of Example 1

The contact material of Example 1 was tested in a manner similar to that used in Comparative Example 2 except that a feed rate of 200 standard cc per minute (double the feed rate used in Comparative Example 2) was used and the contact material bed was diluted with 0.5 grams of diluent instead of 1 gram.

Results:

Oxygen conversion was 100% and methane conversion was 22% to 23%, which is much higher than the methane conversion realized in Comparative Example 2. The selectivity to higher hydrocarbons, e.g., $C_{2+}$ hydrocarbons, was about 61% which is slightly better than that realized in Comparative Example 2. Hydrogen was also produced, but only in quantities sufficient to match that expected from water gas shift reaction. The hydrogen equivalence ratio, i.e., $(H_2—CO_2)/(CO+CO_2)$ was about zero.

In this example, the contact material of the invention wherein alumina is incorporated into the contact material itself (the composition of Example 1) was at least about twice as active as a catalyst prepared by the method of Comparative Example 1 wherein alumina was used as a support.

In addition, hydrogen was produced in sufficient quantities so as to be able to theoretically react with the product carbon dioxide to form carbon monoxide and by-product water with some hydrogen remaining. Such remaining hydrogen can, if desired, be used to convert the carbon monoxide to other useful and desired products, such as through Fischer-Tropsch processing, for example.

A way of showing the amount of hydrogen produced is through an "effective hydrogen to carbon oxides ratio," calculated as $(H_2-CO_2)/(CO+CO_2)$, on a molar basis. This equation subtracts the amount of $CO_2$ produced from the amount of hydrogen produced to account for the $CO_2$ shifting back to CO via the water-gas-shift reaction, i.e., $H_2+CO_2 \rightarrow CO+H_2O$. The amount of hydrogen remaining is then divided by the amount of product CO plus the amount of CO that would result from the shifting back of the produced $CO_2$.

An effective hydrogen-to-carbon oxides ratio of 2 is near the stoichiometric amount of hydrogen needed to form paraffinic products and water (such as by Fischer Tropsch reactions) or to form methanol. At ratios below 2, carbon will have to be rejected or hydrogen added in order to attain ratios of 2. In practice, gases having low effective hydrogen-to-carbon oxides ratios shift CO to $CO_2+H_2$ and reject some $CO_2$. At ratios above 2, additional carbon oxides can be added to the processing stream or the carbon oxides can be added to the processing stream or the carbon oxides can be methanated to methane and water (methanation typically requires a ratio of about 3).

EXAMPLE 3

The contact material of Example 1 was tested in a manner similar to that used in Comparative Example 2 except that the methane of oxygen feed gas ratio was increased to 10:1 by using a blend of 40% methane, 4% oxygen, and the balance nitrogen (on a volume basis). Also for this example, the amount of contact material was reduced ten fold so that only 0.05 grams of contact material was used. By so doing, the relative feed ratio was increased ten fold relative to that of Comparative Example 2.

Results:

With operation at 850° C., oxygen conversion was essentially complete showing that the contact material used in this Example was much more active than the catalyst of Comparative Examples 1 and 2. In Example 3, the selectivity to higher hydrocarbons ($C_{2+}$) was 70% with the balance of carbon being present as carbon oxides. The effective hydrogen to carbon oxide ratio was about 0.4, providing the potential for further conversion of the carbon oxides and hydrogen products.

EXAMPLE 4

The contact material of Example 1 was tested as in Example 3 except that the feed rate was doubled. The temperature was also increased to 875° C.

Results:

Oxygen conversion remained at essentially 100% indicating that the contact material was at least 20 times more active at the same temperature than the catalyst of Comparative Examples 1 and 2. The selectivity to higher hydrocarbons ($C_{2+}$) increased to 75% with the balance of carbon being present as carbon oxides. The effective hydrogen to carbon oxides ratio increased to 0.6. Indicating that potentially more of the carbon oxides produced can be relatively more easily processed to produce more valuable products, as compared to processing resulting in a lower effective hydrogen to carbon oxides ratio.

EXAMPLE 5

The contact material of Example 1 was tested in a manner similar to that of Comparative Example 2 except that 0.100 gram of contact material powder was used and the feed gas, in addition the specified percentages of $CH_4$ and $O_2$, contained 10 volume % $CO_2$ with a corresponding reduction in the amount of nitrogen in the feed.

The feed rate was 200 cc per minute. A series of temperatures (800° C., 825° C., 850° C., 875° C. and 900° C.) were examined. The temperature was maintained at each of the examined levels for a period of 3 hours.

Results:

At 875° C., oxygen conversion was about 93% showing that the presence of $CO_2$ in the feed suppressed the activity of the contact material, but the activity of the material was still extremely high even with the relative feed rate of 120,000 cc of feed gas per gram of contact material. Methane conversion was 23% with a selectivity to $C_{2+}$ hydrocarbons of about 60%. Carbon monoxide and a net amount of $CO_2$ were produced along with hydrogen.

In view of this example, carbon dioxide in the feed can be used to moderate the high activity of this contact material and carbon dioxide does not have to be completely removed from the feed.

At 900° C., complete oxygen conversion was attained with a selectivity to $C_{2+}$ hydrocarbons of 60% and a methane conversion of 23-24% per pass.

Example 6

Contact Material Stability

The stability of the contact material of Example 1 under oxidative coupling reaction conditions for methane conversion was examined in the following manner:

A 0.050 gram portion of the contact material of Example 1, in the form of a fine powder of 100-180 mesh, was diluted with an inert diluent solid in a weight ratio of 10:1 and loaded in a quartz reactor, forming a contact material zone. A feed gas blend of 40 volume % methane, 4 volume % oxygen and the balance nitrogen was passed over the contact material-diluent mass at the relative feed rate of 120,000 standard cc-gas per hour per gram of contact material.

A series of operating temperatures (750° C., 775° C., 800° C., 825° C., 850° C. and 875° C.) for the contact material zone were investigated with the operating temperature held at each of the selected temperatures for about 3 hours followed by a return to room temperature. FIG. 1 shows the methane and oxygen conversion and $C_{2+}$ selectivity at the various, selected operating temperatures. The highest $C_{2+}$ selectivity was realized at the highest temperature examined, i.e., 875° C.

To examine the stability of the contact material over an extended operating time period, the contact material zone temperature was brought to 875° C. and, using a relative feed rate of 240,000 standard cc-gas per hour per gram of contact material, held constant at these operating conditions for 2 days of operation.

Results:

The stability of the contact material is illustrated by FIG. 2 which shows that there was no significant change in the performance of the contact material as demonstrated by the maintenance of the $C_{2+}$ selectivity and oxygen and methane conversion levels during the duration of the test period, showing the stable behavior of the contact material. Further, even at the higher feed rate used in this stability testing, the $O_2$ conversion was essentially 100%, indicating a contact material of very high activity.

Example 7

Larger scale sol-gel preparation followed by spray drying

Physical requirements for a fluidizable contact material include appropriate particle size and attrition resistance. Fluidizable contact materials are typically spray dried. A spray dried contact material with a nominal composition of $YBa_2AlO_x$, where x=molar amount, necessary for the composition to be at stoichiometric balance was prepared in the following manner:

A yttria sol (51.40 lbs.) from Nyacol Products Inc. was blended with a PHF alumina sol (40.60 lbs.) using a homogenizer. A barium hydroxide solution (40.10 lbs. BaOH/43 l water), heated to 50° C., was added to this mixture while mixing. As a gel thickened, an additional 30 gallons of water were added to the gel mixture to dilute the thickness of the gel. The resulting gel was thoroughly blended with the homogenizer. The material from the homogenizer was spray-dried and collected.

The fines and large particle bulk material were reslurried and spray-dried a second time to increase the total yield of fluidizable contact material. The material was placed directly in an oven at 800° C. and calcined in flowing air for 5 hours.

General Guidelines Re Particle Size:

The average particle size range for the fluidizable material will typically be about 30 to 125 microns, with a median fluidizable particle size of about 72 to 75 microns.

| Typical Size Distribution Particle Size (Microns) | Weight Percent |
|---|---|
| 80+ | 25 |
| 40–80 | 60 |
| 20–40 | 15 |
| 0–20 | ≦1 |

Example 8

The fluidizable $YBa_2AlO_x$ contact material of Example 7 was loaded into a fixed bed reactor unit using a gaseous feed stream containing 30 volume % $CH_4$, 6 volume % $O_2$, and the balance being $N_2$ gas and a feed rate of 150,000 cc of feed at ambient conditions per hour per gram of contact material for runs at 750° C. and 850° C.

The results are given in Table 1 below.

TABLE 1

| Temperature (°C.) | 750 | 800 | 850 |
|---|---|---|---|
| Methane Conversion (%) (in-out) | 18.2 | 21.9 | 21.7 |
| Oxygen conversion (%) | 86 | 98 | 99 |

TABLE 1-continued

| Temperature (°C.) | 750 | 800 | 850 |
|---|---|---|---|
| $C_{2+}$ selectivity (%) | 52.5 | 61.8 | 63.0 |
| $CO_2$ selectivity (%) | 35 | 32 | 31 |
| CO selectivity (%) | 12 | 6 | 6 |

Discussion of Results:

The spray dried contact material of Example 7 was highly active as shown by the 99% oxygen conversion realized at 850° C., with a relative feed ratio of 150,000 cc/gm-hr versus the results obtained in Comparative Example 2 in the testing of the material of Comparative Example 1, wherein oxygen conversion was only about 38%.

In addition, selectivity to $C_{2+}$ hydrocarbons for the spray dried contact material of Example 7 was 63%, as compared to the $C_{2+}$ hydrocarbon selectivity of only 58% in Comparative Example 2.

As shown in Example 8, the performance of the spray dried material of Example 7 was comparable (in terms of activity and selectivity) to the sol-gel preparation of Example 1 (tested in Example 2).

Examples 9 and 10

In these examples, the contact material of Example 1 was used in an oxidative conversion process, using n-butane as a feedstock, to produce dehydrogenated and lighter products.

In both examples, the contact material was tested in a tubular fixed bed quartz reactor with inert alpha alumina packed in the heated pre- and post-contact material zones. The reaction temperature was measured via a quartz thermowell. The feedstock gas was 4 volume % oxygen and 4 volume % n-butane with the balance of the feedstock gas being inert nitrogen.

In Example 9, the contact material was tested in a once-through mode of operation, with no recycle.

In Example 10, the contact material was tested with recycle using an external pump between the reactor effluent and inlet streams.

Tables 2 and 3 identify the reaction conditions and conversion and selectivity results, respectively, for Examples 9 and 10.

TABLE 2

| REACTION CONDITIONS | | |
|---|---|---|
| Temperature (°C.) | Example 9 700 | Example 10 700 |
| Pressure (atm) | 1 | 1 |
| Feed Rate (sccm) | 100 | 50 |
| Recycle Rate (sccm) | — | 1000 |
| Catalyst Weight (g) | 0.2 | 0.2 |

TABLE 3

| CONVERSION AND SELECTIVITY RESULTS | | |
|---|---|---|
| | Example 9 | Example 10 |
| Conversion of n-butane, C % | 66.0 | 77.5 |
| Selectivity, C % | | |
| Carbon Moxoxide | 7.5 | 9.9 |
| Carbon Dioxide | 12.1 | 14.0 |
| Methane | 12.2 | 17.7 |
| Ethene | 36.9 | 49.6 |
| Ethane | 1.7 | 2.3 |
| Propene | 23.4 | 6.2 |
| Propane | 0.4 | 0.3 |
| cis-Butene-2 | 0.9 | — |
| trans-Butene-2 | 1.1 | — |
| Butene-1 | 1.9 | — |
| 1,3-Butadiene | 1.9 | — |

TABLE 3-continued

| CONVERSION AND SELECTIVITY RESULTS | | |
|---|---|---|
| | Example 9 | Example 10 |
| Selectivity to $H_2$, mol % | 12.8 | 13.5 |
| Carbon Mass Balance, % | 104.0 | 107.4 |

(* = mole of hydrogen produced per mole of hydrogen in the converted butane)

Discussion of Results:

As shown in Table 3, Examples 9 and 10 resulted in significant conversion of n-butane to ethene and propene, which are both high-valued chemical feedstocks. By controlling the mode of operation (e.g., with or without recycle), both n-butane conversion and ethene selectivity can be favorably affected.

The foregoing detailed description is given for clearness of understanding only, and no unnecessary limitations are to be understood therefrom, as modifications within the scope of the invention will be obvious to those skilled in the art.

That which is claimed is:

1. A composition which comprises an intimately mixed, mixed oxide of:

a) at least one cationic species of a naturally occurring Group IIIB element;
   b) at least one cationic species of a Group IIA metal selected from the group consisting of magnesium, calcium, strontium and barium; and
   c) a cationic species of aluminum.

2. The composition of claim 1 wherein the Group IIIB element is selected from the group consisting of yttrium, lanthanum, neodymium, samarium and ytterbium.

3. The composition of claim 2 wherein the Group IIIB element is yttrium.

4. The composition of claim 1 wherein the Group IIA metal is strontium.

5. The composition of claim 1 wherein the Group IIA metal is barium.

6. The composition of claim 1 wherein the material comprises about 2 to about 20 wt. % aluminum, on an elemental basis.

7. The composition of claim 6 wherein the material comprises about 5 to about 10 wt. % aluminum, on an elemental basis.

8. The composition of claim 1 wherein the material comprises, in an approximate molar ratio, about 1 Group IIIB metal to about 0.5–3 Group IIA metal.

* * * * *